United States Patent [19]

McMillan et al.

[11] Patent Number: 5,399,481
[45] Date of Patent: Mar. 21, 1995

[54] METHODS AND COMPOSITIONS FOR DIAGNOSING CHRONIC IMMUNE THROMBOCYTOPENIC PURPURA

[75] Inventors: Robert McMillan, Del Mar; Mark H. Ginsberg, San Diego, both of Calif.; Edward F. Plow, Solon, Ohio

[73] Assignee: The Scripps Research Institute, La Jolla, Calif.

[21] Appl. No.: 998,361

[22] Filed: Dec. 29, 1992

Related U.S. Application Data

[60] Division of Ser. No. 803,624, Nov. 27, 1991, which is a continuation-in-part of Ser. No. 620,669, Dec. 3, 1990, Pat. No. 5,177,188.

[51] Int. Cl.$^6$ .................. G01N 33/53; C07K 7/08; C07K 7/10; C07K 7/06
[52] U.S. Cl. .................. 435/7.1; 435/7.92; 435/975; 530/324; 530/325; 530/326; 530/806; 530/810
[58] Field of Search .............. 435/7.1, 975, 7.92; 530/324, 325, 806, 810, 326

[56] References Cited

U.S. PATENT DOCUMENTS 4,810,632 3/1989 McMillan .

FOREIGN PATENT DOCUMENTS

WO90/00178 1/1990 WIPO .

OTHER PUBLICATIONS

Beardsley, et al., *J. Clin. Invest.* 74: 1701–1707 (1984).
Fitzgerald, et al., *J. Biol. Chem.* 262: 3936–3939 (1987).
Kekomaki, et al., *Blood* 74 (Suppl. 1): 91a, No. 337 (1989).
McMillan, *NEJM* 304: 1135–1147 (1981).
Zimrin, et al., *J. Clin. Invest.* 81: 1470–1475 (1988).
Nakajima, et al., *Chem. Abst.* 108: 73568z (1988).
O'Toole, et al., *Blood* 74: 14–18 (1989).
Frelinger, et al., *J. Biol. Chem.* 265: 6346–6352 (1990).

*Primary Examiner*—George C. Elliott
*Attorney, Agent, or Firm*—April C. Logan

[57] ABSTRACT

The present invention discloses polypeptides consisting essentially of an amino acid residue sequence corresponding to a formula selected from the group consisting of: Tyr-His-Asp-Arg-Lys-Glu-Phe-Ala-Lys-Phe-Glu-Glu-Glu-Arg-Ala-Arg-Ala-Lys-Trp-Asp-Thr-Ala-Asn-Asn (SEQ ID NO 1); Ala-Asn-Asn-Pro-Leu-Tyr-Lys-Glu-Ala-Thr-Ser-Thr-Phe-Thr-Asn-Ile-Thr-Tyr-Arg-Gly-Thr (SEQ ID NO 2); Ile-His-Asp-Arg-Lys-Glu-Phe-Ala-Lys-Phe-Glu-Glu-Glu-Arg-Ala-Arg-Ala-Lys-Trp-Asp-Thr-Ala-Asn-Asn-Pro-Leu-Tyr-Lys-Glu-Ala-Thr-Ser-Thr-Phe-Thr-Asn-Ile-Thr-Tyr-Arg-Gly-Thr (SEQ ID NO 4); and Gly-Pro-Asp-Ile-Leu-Val-Val-Leu-Leu-Ser-Val-Met-Gly-Ala-Ile-Leu-Leu-Thr-Gly-Leu-Ala-Ala-Leu-Leu-Ile-Trp-Lys-Leu-Leu-Ile-Thr-Ile-His-Asp-Arg-Lys-Glu-Phe-Ala-Lys-Phe-Glu-Glu-Glu-Arg-Ala-Arg-Ala-Lys-Trp-Asp-Thr-Ala-Asn-Asn-Pro-Leu-Tyr-Lys-Glu-Ala-Thr-Ser-Thr-Phe-Thr-Asn-Ile-Thr-Tyr-Arg-Gly-Thr (SEQ ID NO 5), as well as diagnostic kits including same. The present invention also discloses methods for determining the presence of anti-GPIIIa autoantibodies in a vascular fluid sample, which autoantibodies are indicative of chronic immune thrombocytopenic purpura in a patient.

6 Claims, 4 Drawing Sheets

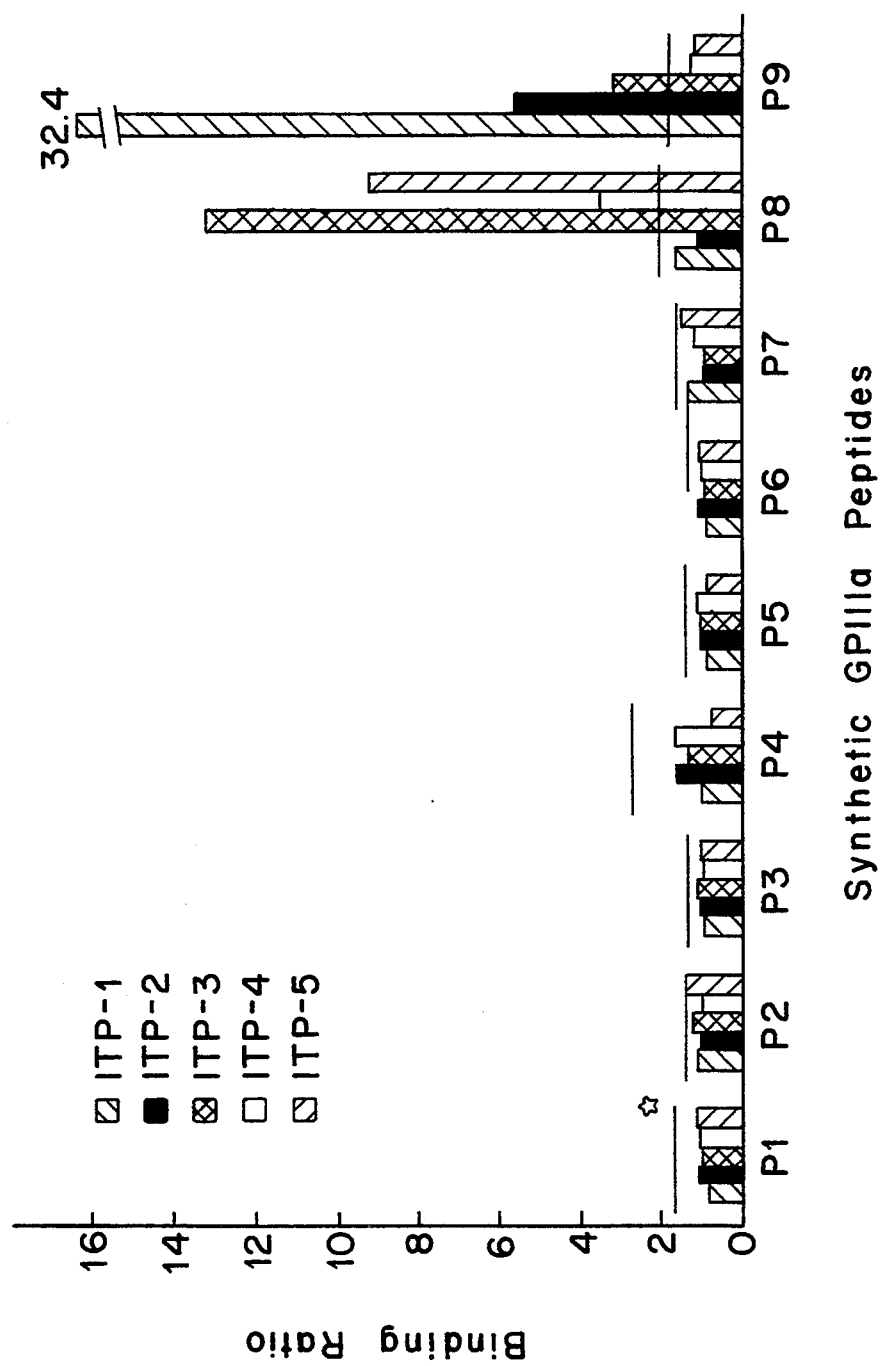

5,399,481

METHODS AND COMPOSITIONS FOR DIAGNOSING CHRONIC IMMUNE THROMBOCYTOPENIC PURPURA

This invention was made with the support of the United States Government under National Institutes of Health Grants HL 28235, HL 37945, HL 38292, and HL 16411. The government may have certain rights in the invention.

CROSS REFERENCE TO RELATED APPLICATIONS

The present application is a divisional of copending U.S. application Ser. No. 07/803,624, filed Nov. 27, 1991, which is a continuation-in-part of application Ser. No. 07/620,669, filed Dec. 3, 1990 (now U.S. Pat. No. 5,177,188), the disclosure of which are incorporated by reference herein.

TECHNICAL FIELD

The present invention relates to polypeptides useful in detecting anti-GPIIIa autoantibodies indicative of chronic immune thrombocytopenic purpura.

BACKGROUND

Chronic immune thrombocytopenic purpura (ITP) is an autoimmune disorder characterized by thrombocytopenia due to the production of antiplatelet autoantibodies which result in platelet destruction by the reticuloendothelial system or inhibition of platelet production (McMillan, *N. Engl. J. Med.*, 304:1135-1147, 1981; Kelton et al., *Semin. Thromb. Haemost.*, 8:83-104, 1982). Autoantibody from approximately three-fourths of these patients is known to react with the membrane glycoprotein (GP) complexes —GPIIb/IIIa or GPIb-/IX (van Leeuwen et al., *Blood*, 59:23-26, 1982; Woods et al., *Blood*, 63:368-375, 1984; Woods et al., *Blood*, 64:156-160, 1984; Beardsley et al., *J. Clin. Invest.*, 74:1701-1707, 1984; McMillan et al., *Blood*, 70:1040-1045, 1987); of these, some have been shown to bind to GPIIIa (Beardsley et al., *J. Clin. Invest.*, 74:1701-1707, 1984). However, little information is available on the precise location of epitopes on GPIIIa. A recent abstract by Kekomaki et al. showed that plasma from one ITP patient, which reacted with GPIIIa by immunoblotting, bound to a 60,000 dalton GPIIIa fragment resulting from chymotrypsin digestion (Kekomaki et al., *Blood*, 74:91, 1989).

BRIEF SUMMARY OF THE INVENTION

Polypeptides capable of immunologically mimicking GPIIIa cytoplasmic domain epitopes recognized by autoantibodies indicative of chronic ITP have now been discovered.

Thus, in one embodiment, the present invention contemplates a polypeptide of less than about 120 residues having an amino acid residue sequence that includes a sequence corresponding to a formula selected from the group consisting of:

Tyr—His—Asp—Arg—Lys—Glu—Phe—Ala—Lys—Phe—Glu—
Glu—Glu—Arg—Ala—Arg—Ala—Lys—Trp—Asp—Thr—Ala—
Asn—Asn (SEQ ID NO 1);

Ala—Asn—Asn—Pro—Leu—Tyr—Lys—Glu—Ala—Thr—
Ser—Thr—Phe—Thr—Asn—Ile—Thr—Tyr—Arg—
Gly—Thr (SEQ ID NO 2);

-continued
Ile—His—Asp—Arg—Lys—Glu—Phe—Ala—Lys—Phe—
Glu—Glu—Glu—Arg—Ala—Arg—Ala—Lys—Trp—Asp—
Thr—Ala—Asn—Asn—Pro—Leu—Tyr—Lys—Glu—Ala—
Thr—Ser—Thr—Phe—Thr—Asn—Ile—Thr—Tyr—Arg—
Gly—Thr (SEQ ID NO 4);

and

Gly—Pro—Asp—Ile—Leu—Val—Val—Leu—Leu—Ser—Val—
Met—Gly—Ala—Ile—Leu—Leu—Thr—Gly—Leu—Ala—Ala—
Leu—Leu—Ile—Trp—Lys—Leu—Leu—Ile—Thr—Ile—His—
Asp—Arg—Lys—Glu—Phe—Ala—Lys—Phe—Glu—Glu—Glu—
Arg—Ala—Arg—Ala—Lys—Trp—Asp—Thr—Ala—Asn—Asn—
Pro—Leu—Tyr—Lys—Glu—Ala—Thr—Ser—Thr—Phe—Thr—
Asn—Ile—Thr—Tyr—Arg—Gly—Thr (SEQ ID NO 5).

In another embodiment a polypeptide of this invention has an amino acid residue sequence corresponding to the formula:

Tyr—His—Asp—Arg—Lys—Glu—Phe—Ala—Lys—Phe—
Glu—Glu—Glu—Arg—Ala—Arg—Ala—Lys—Trp—Asp—
Thr—Ala—Asn—Asn—Ala—Asn—Asn—Pro—Leu—Tyr—
Lys—Glu—Ala—Thr—Ser—Thr—Phe—Thr—Asn—Ile—
Thr—Tyr—Arg—Gly—Thr (SEQ ID NO 3).

The present invention further contemplates a method for determining the presence of anti-GPIIIa autoantibodies in a vascular fluid sample, said autoantibodies being indicative of chronic immune thrombocytopenic purpura in a patient. The method comprises admixing a vascular fluid sample from a patient with a polypeptide of this invention to form an immunoreaction admixture. The admixture thus formed is maintained under biological assay conditions for a period of time sufficient to form an immunoreaction product containing the polypeptide. The presence of the immunoreaction product, and thereby the presence of said anti-GPIIIa autoantibodies is then determined.

BRIEF DESCRIPTION OF THE DRAWINGS

In the drawings forming a portion of this disclosure:

FIG. 1 illustrates autoantibody binding to synthetic GPIIIa peptides. Microtiter wells coated with synthetic GPIIIa peptides are incubated with test plasma. Well-bound autoantibody is detected using radiolabeled anti-human IgG. Binding ratio equals cpm binding to test peptide/cpm binding to control peptide. Horizontal bar designates 3 standard deviations above the mean binding ratios of 18 control plasmas.

DETAILED DESCRIPTION OF THE INVENTION

A. Definitions

Figure 2A:
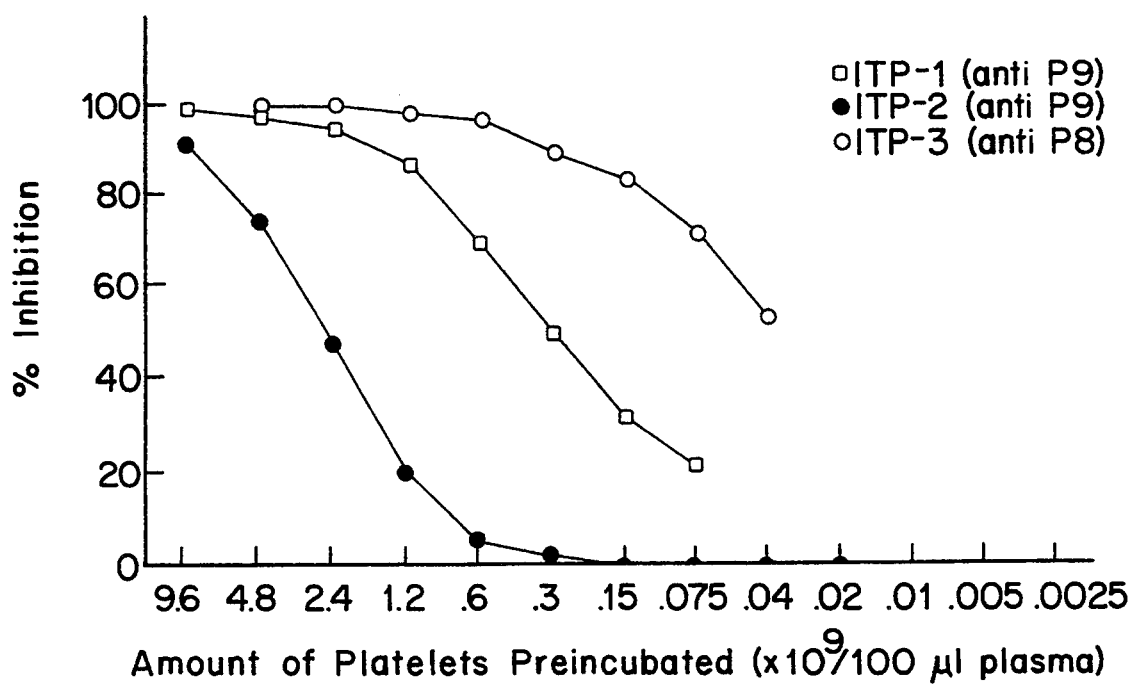
FIGS. 2A and 2B illustrate inhibition of antipeptide antibody binding by platelets and affinity-purified GPIIb/IIIa. Plasma (1/10 dilution) from patients ITP 1-3 was preincubated with either washed platelets (FIG. 2A) or purified GPIIb/IIIa (FIG. 2B) and then reacted with GPIIIa peptides. Results are expressed as the % inhibition.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in J. Biol. Chem., 243:3552–59 (1969) and adopted at 37 C.F.R. §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822(b)(4), and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxy-terminal group such as COOH.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Protein: refers to a linear series of greater than 50 amino acid residues connected one to the other as in a polypeptide.

Synthetic peptide: refers to a chemically produced chain of amino acid residues linked together by peptide bonds that is free of naturally occurring proteins and fragments thereof.

B. Polypeptides

The present invention contemplates a polypeptide that immunoreacts with anti-GPIIIa autoantibodies. A polypeptide of the present invention is further characterized as having an amino acid residue sequence that includes an amino acid residue sequence represented by one of the following formulae:

| Formula Designation | SEQ ID NO | Sequence[1] |
|---|---|---|
| P8 | 1 | YHDRKEFAKFEEERARAKWDTANN |
| P9 | 2 | ANNPLYKEATSTFTNITYRGT |
| P89 | 3 | YHDRKEFAKFEEERARAKWDTANN-ANNPLYKEATSTFTNITYRGT |
| p(721-762) | 4 | IHDRKEFAKFEEERARAKWDTANN-PLYKEATSTFTNITYRGT |
| p(690-762) | 5 | GPDILVVLLSVMGAILLTGLAALL-IWKLLITIHDRKEFAKFEEERARA-KWDTANNPLYKEATSTFTNITYRGT |

[1]The amino acid residue sequence is shown in single letter code, and a dash at the end of a line indicates that the sequence continues on the next line.

In a preferred embodiment, a polypeptide of this invention contains, and preferably consists essentially of, the amino acid residue sequence according to one of the above formulas shown in Table 1.

In another embodiment, subject polypeptide is characterized by the presence of a plurality of GPIIIa segments (regions) within the polypeptide's primary structure, each of the segments being defined by a sequence of amino acid residues corresponding to one of the formulae P8, P9, P89, p(690-762) or p(721-762).

The GPIIIa-derived segments can be adjacent and/or contiguous within the polypeptide chain, with adjacent segments being separated in the amino acid residue sequence of the polypeptide by one or more spacing residue. Preferably, the spacing residues make up a spacing segment in the range of about 1 to about 20, preferably about 5 to about 15, and more usually about 10, amino acid residues in length.

In addition, a subject polypeptide can contain a leader segment of 1 conveniently up to about 33, such as about 11, about 18 or about 22, amino acid residues located amino-terminal to the amino-terminal GPIIIa-derived or spacing segment.

In a similar manner, a subject polypeptide need not end with the carboxy-terminal residue of a GPIIIa-derived segment or spacer segment. A carboxy terminal tail segment can be present containing 1 conveniently up to about 33, such as about 11, about 18 or about 22, amino acid residues.

Preferred polypeptides of the present invention are therefore defined by formulas I, II, III, IV or V:

Formula I

B—(Xaa$_n$—Tyr—His—Asp—Arg—Lys—Glu—Phe—Ala—Lys—Phe—Glu—Glu—Glu—Arg—Ala—Arg—Ala—Lys—Trp—Asp—Thr—Ala—Asn—Asn—Xaa$_m$)$_a$—J (SEQ ID NO 6);

Formula II

B—(Xaa$_n$—Ala—Asn—Asn—Pro—Leu—Tyr—Lys—Glu—Ala—
Thr—Ser—Thr—Phe—Thr—Asn—Ile—Thr—Tyr—Arg—Gly—
Thr—Xaa$_m$)$_a$—J (SEQ ID NO 7);

Formula III

B—(Xaa$_n$—Ile—His—Asp—Arg—Lys—Glu—Phe—Ala—
Lys—Phe—Glu—Glu—Glu—Arg—Ala—Arg—Ala—Lys—Trp—
Asp—Thr—Ala—Asn—Asn—Pro—Leu—Tyr—Lys—Glu—Ala—
Thr—Ser—Thr—Phe—Thr—Asn—Ile—Thr—Tyr—Arg—Gly—
Thr—Xaa$_m$)$_a$—J (SEQ ID NO 8);

and

Formula IV

B—(Xaa$_n$—Gly—Pro—Asp—Ile—Leu—Val—Val—Leu—
Leu—Ser—Val—Met—Gly—Ala—Ile—Leu—Leu—Thr—Gly—
Leu—Ala—Ala—Leu—Leu—Ile—Trp—Lys—Leu—Leu—Ile—
Thr—Ile—His—Asp—Arg—Lys—Glu—Phe—Ala—Lys—Phe—
Glu—Glu—Glu—Arg—Ala—Arg—Ala—Lys—Trp—Asp—Thr—
Ala—Asn—Asn—Pro—Leu—Tyr—Lys—Glu—Ala—Thr—Ser—
Thr—Phe—Thr—Asn—Ile—Thr—Tyr—Arg—Gly—Thr—
Xaa$_m$)$_a$—J (SEQ ID NO 9).

In the above formulae, B is an amino-terminal NH$_2$ group or a previously discussed leader segment; J is a carboxy-terminal COOH group or a previously discussed tail segment; Xaa represent spacing segments whose amino acid residue sequences can be the same or different; n is either 1 or 0 such that when n is 1, Xaa is present, and when n is 0, Xaa is not present; m is either 1 or 0 such that when m is 1, Xaa is present, and when m is 0, Xaa is not present; and a is an integer from 2 to about 10, more preferably 2 to about 5 and usually 2 to 3, indicating the number of times the amino acid residue sequence in parenthesis is present (repeated) in the polypeptide primary structure. Preferably, the sequence in parenthesis corresponds in its entirety, and preferably is identical to, a portion of the amino acid residue sequence of GPIIIa.

In addition, in the above formula I, a substitution of the tyrosine residue (Tyr) at the beginning of the specified sequence that corresponds to position 721 of P8 is contemplated such that an isoleucine (Ile) residue is at that position in place of Tyr. Isoleucine is the residue normally found in native GPIIIa at residue position 721.

A subject polypeptide typically contains a total of about 20 to about 450 amino acid residues, preferably less than about 120 residues. Typically, a subject polypeptide contains no more than about 100, preferably no more than about 70 and usually no more than about 20 or 40 amino acid residues in its primary sequence. The preferred limitation on polypeptide size is primarily due to the size and purity limitations on synthetic polypeptides presented by current technologies, and is also due to the increased immunospecificity afforded by presenting a smaller region of GPIIIa.

A subject polypeptide includes any analog, fragment or chemical derivative of a polypeptide whose amino acid residue sequence is shown herein so long as the polypeptide is capable of immunoreacting with GPIIIa autoantibodies indicative of chronic ITP. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability to mimic a GPIIIa epitope as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

A subject polypeptide can be prepared using recombinant nucleic acid methodologies well known in the art. For instance, DNA sequences useful in producing a subject polypeptide are described in Paik et al., *Proc. Natl. Acad. Sci. USA*, 82:3445-3449, (1985); McLean et al., *J. Biol. Chem.*, 259:6498-6504, (1984); and Rall et al., *J. Biol. Chem.*, 257:4171-4178, (1982). A DNA segment coding for a polypeptide of this invention can be synthesized by chemical techniques, for example the phosphotriester method of Matteucci et al., *J. Am. Chem. Soc.*, 103:3185, (1981). The DNA segment can then be ligated into an expression vector, and a host transformed therewith can be used to produce the polypeptide. See, for example, *Current Protocols In Molecular Biology*, Ausubel et al., eds., John Wiley & Sons, New York, N.Y.; U.S. Pat. No. 4,237,224, No. 4,356,270, No. 4,468,464, No. 4,683,195 and No. 4,889,818.

The recombinant expression vectors capable of expressing a subject polypeptide and methods of their use for producing a subject polypeptide are contemplated as part of the present invention.

A subject polypeptide can also be prepared using the solid-phase synthetic technique initially described by Merrifield, in J. Am. Chem. Soc., 85:2149–2154 (1963). Other polypeptide synthesis techniques may be found, for example, in M. Bodanszky et al., Peptide Synthesis, John Wiley & Sons, 2d Ed., (1976) as well as in other reference works known to those skilled in the art. A summary of polypeptide synthesis techniques may be found in J. Stuart and J. D. Young, Solid Phase Peptide Synthesis, Pierce Chemical Company, Rockford, Ill., 3d Ed., Neurath, H. et al., Eds., p. 104–237, Academic Press, New York, N.Y. (1976). Appropriate protective groups for use in such syntheses will be found in the above texts as well as in J. F. W. McOmie, Protective Groups in Organic Chemistry, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

The preparation of therapeutic compositions which contain polypeptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Anti-Polypeptide Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See, for example, U.S. Pat. No. 4,342,566 to Theofilopolous and Dixon. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

An antibody of the present invention immunoreacts with a subject polypeptide, preferably a polypeptide according to formula P8, P9, P89, p(690–762), p(721–762), Formula I, Formula II, Formula III or Formula IV. The antibody is further characterized as not immunoreacting with a polypeptide according to formula P1, P2, P3, P4, P5, P6, and P7 as shown in Table 1. In preferred embodiments, the antibody does not immunoreact with GPIIIa present on the surface of platelets. Useful methods for determining the ability of an antibody to react with antigens on the surface of platelets are described in U.S. Pat. No. 4,810,632.

A subject antibody is typically produced by immunizing a mammal with an inoculum containing a polypeptide according to formula P8, P9, P89, p(721-762), Formula I, Formula II, Formula III or Formula IV. Antipolypeptide antibody molecules induced by the inoculum are then collected from the mammal. Methods useful for producing and characterizing anti-polypeptide antibodies are described in U.S. Pat. No. 4,663,436 and No. 4,493,795.

To enhance the antibody specificity, antibodies that are purified by immunoaffinity chromatography using solid phase-affixed immunizing polypeptide are preferred. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The antibody so produced can be used, inter alia, in the diagnostic methods and systems of the present invention to detect anti-GPIIIa autoantibodies indicative of chronic ITP present in a body sample.

The word "inoculum" in its various grammatical forms is used herein to describe a composition containing a polypeptide of this invention as an active ingredient used for the preparation of antibodies immunoreactive with said polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein, et al., *J. Infect. Dis.*, 147:318-326 (1983) and the like, or the use of carbodiimide technology as in the use of a water-soluble carbodiimide to form amide links to the carrier. For a review of protein conjugation or coupling through activated functional groups, see Avrameas, et al., *Scand. J. Immunol.*, 1:7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine; D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Aurameas, et al., *Scand. J. Immunol.*, Vol. 8, Suppl. 7:7-23 (1978) and U.S. Pat. No. 4,493,795, No. 3,791,932 and No. 3,839,153. In addition, a site directed coupling reaction can be carried out so that any loss of activity due to polypeptide orientation after coupling can be minimized. See, for example, Rodwell et al., *Biotech.*, 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

D. Assay Methods

Useful solid and liquid phase assay methods are discussed herein. However, the invention is not so limited. Further, while the particularly described assay methods utilize a radio-label, the present invention is not specifically limited to such assays. Additional assay methods are described hereinbelow with particular emphasis on solid phase immunoassay methods.

Those skilled in the art will understand that there are numerous methods of solid phase immunoassays that may be utilized herein. Exemplary, useful solid phase assays include enzyme multiplied immunoassay techniques (EMIT) and fluorescence immune assays (FIA), in addition to the specifically discussed RIA, solid phase radioimmunoassay (SPRIA) of Example 8B, and ELISA. However, any method that results in a signal imparted by the reaction of autoantibodies with a polypeptide of this invention is considered. Each of those assay methods can employ single or double antibody techniques in which an indicating means is utilized to signal the immunoreaction, and thereby the binding of an autoantibody that is to be assayed with a polypeptide of this invention. Exemplary techniques can be found explained in Maggio, *Enzyme Immunoassay*, CRC Press, Cleveland, Ohio (1981); and in Goldman, *Fluorescent Antibody Methods*, Academic Press, New York, N.Y. (1980).

A vascular fluid sample is utilized in this assay method. The sample is typically either serum or plasma.

One contemplated assay method determines the presence, and preferably the amount of anti-GPIIIa autoantibodies in a vascular fluid sample. This method includes the following steps.

(a) A vascular fluid sample is admixed with a subject polypeptide to form an immunoreaction admixture. The polypeptide preferably is operatively linked to a solid support such that the immunoreaction admixture has both a liquid phase and a solid phase.

(b) The immunoreaction admixture is maintained under biological assay conditions for a time period, typically predetermined, sufficient to form a polypeptide-containing immunoreaction product in the solid phase. In heterogeneous assay formats, the reactants are usually separated after the maintenance period, typically by washing and retaining the solid-phase.

(c) The presence, and preferably the amount of immunoreaction product formed in step (b) and thereby the presence or amount of anti-GPIIIa autoantibodies in the vascular fluid sample is then determined.

Biological assay conditions are those conditions that are able to sustain the biological activity of the immunochemical reagents of this invention and the antigen sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art.

In a preferred embodiment of the above method the amount of immunoreaction product is determined according to step (c) by (i) admixing a labeled specific binding agent capable of binding the polypeptide-containing immunoreaction product to form a labeling reaction admixture, (ii) maintaining the labeling reaction admixture under biological assay conditions for a time period sufficient for the labeled specific binding agent to bind the polypeptide-containing immunoreaction product to form a labeled complex, and (iii) detecting the presence or amount of any labeled complex formed, and thereby detecting the presence or amount of anti-GPIIIa autoantibody-containing immunoreaction product.

In a particularly preferred embodiment, the labeled specific binding agent is labelled anti-IgG.

In another embodiment, the vascular fluid sample is immunoreacted with a subject polypeptide in labeled and unlabeled forms. Typically, the unlabeled polypeptide is attached to a solid matrix. One arm of the autoantibody will bind the solid-phase polypeptide and another arm of the antibody will bind the labeled polypeptide, thereby forming a solid-phase labeled immunoreaction product. Immunoreactions with the labeled and unlabeled polypeptide can be performed substantially concurrently, i.e., in the same admixture, or serially.

In another embodiment, a subject polypeptide is simultaneously immunoreacted with an anti-polypeptide antibody of this invention and the vascular fluid sample. Preferably, the polypeptide is affixed to the solid support and the anti-polypeptide antibody is labeled. Alternatively, the anti-polypeptide antibody is affixed to the solid support and the polypeptide is labeled. In either case, a labeled solid-phase immunoreaction product is formed that is indicative of the presence and/or amount of anti-GPIIIa autoantibodies.

Preferably, non-specific protein binding sites on the surface of the solid phase support are blocked. Thus, the solid phase-bound polypeptide is bound as by adsorption or other well known means of affixation to the solid matrix. Thereafter, an aqueous solution of a protein free from interference with the assay such as bovine, horse or other serum albumin that also is free from contamination with GPIIIa is admixed with the solid phase to adsorb the admixed protein onto the surface of the polypeptide-containing solid support at protein binding sites on the surface that are not occupied by the monoclonal paratopic molecule.

A typical aqueous protein solution contains about 3 to about 10 weight percent bovine serum albumin in PBS at a pH value of 7.1–7.5. The aqueous protein solution-solid support admixture is typically maintained for a time period of at least one hour at 37° C., and the resulting solid phase is thereafter rinsed free of unbound protein.

The vascular fluid sample can be plasma or serum, as already noted. The sample is preferably diluted at about 1:10 to about 1:5000, and more preferably at about 1:10.

E. Diagnostic Systems

The present invention also contemplates a diagnostic system, typically in kit form, that can be utilized in carrying out the before-described assay methods. The system includes, in an amount sufficient for at least one assay, a subject polypeptide as a separately packaged immunochemical reagent. Instructions for use of the packaged reagent are also typically included.

In one embodiment, a diagnostic system in kit form includes a solid support comprising a solid matrix such as a microtiter plate having a polypeptide of this invention affixed thereto (operatively linked to the solid matrix) in an amount sufficient to carry out at least one assay.

In preferred embodiments, the above diagnostic system further includes, as a separately packaged reagent, a second antibody, a reveal antibody, that contains antibody molecules that immunoreact with human IgG. The system can further include, as a separately packaged reagent, an anti-polypeptide antibody of this invention for use in a competition ELISA format.

Preferably, when the label is an enzyme, a diagnostic system further includes one or more of the following: (i) a supply of hydrogen peroxide of known concentration; (ii) a visualizing oxidative dye precursor such as OPD;

(iii) a solution of a stopping agent such as 4N sulfuric acid to quench the color-forming reaction; (iv) one or more buffers in dry or liquid form for use in the assay; and (v) materials for preparing standard reference curves.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulfonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{11}$indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of anti-GPIIIa antibodies, particularly GPIIIa autoantibodies, in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

A reagent is typically affixed to a solid matrix by adsorption from an aqueous medium although other modes of affixation applicable to proteins and polypeptides well known to those skilled in the art, can be used.

Thus, in preferred embodiments, a polypeptide, or anti-polypeptide antibody molecule, of the present invention can be affixed in a solid matrix to form a solid support that comprises a package in the subject diagnostic system.

Useful solid matrices are also well known in the art for preparing a solid support containing a reagent affixed thereto. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

EXAMPLES

The following examples are intended to illustrate, but not limit, the present invention.

1. Patients

Plasma from 13 patients with chronic ITP was analyzed. All chronic ITP patients had both platelet-associated and plasma autoantibody directed against platelet membrane GPIIb/IIIa (Beardsley et al., *J. Clin. Invest.*, 74:1701-1070, 1984). In addition, each reacted with GPIIb-IIIa attached to microtiter wells by a monoclonal antibody (Woods et al., *Blood*, 63:368-375, 1984; Woods et al., *Blood*, 64:156-160, 1984) and with affinity-purified GPIIb/IIIa (McMillan, *Trans. Med. Rev.*, 4:136-143, 1990). Chronic ITP patients meeting these criteria represent about 10% of a random ITP population (McMillan et al., *Blood*, 70:1040-1045, 1987).

Also studied were plasma from 3 patients with post-transfusion purpura caused by anti-PLA1 antibody know to bind to GPIIIa, 1 patient with thrombasthenia and post-transfusion anti-GPIIb/IIIa alloantibodies, 1 patient with anti-HLA antibody, 4 patients with nonimmune thrombocytopenia (congestive splenomegaly, aplastic anemia, chronic lymphoid leukemia, glioblastoma on chemotherapy) and 18 normal donors.

2. Preparation of Synthetic Peptides

The amino acid sequence of human GPIIIa, reported by Fitzgerald et al. (Fitzgerald et al., *J. Biol. Chem.*, 262:3936-3939, 1987) was used as the basis for production of synthetic peptides. Peptides were prepared with an Applied Biosystems synthesizer, Model 430 (Foster City, Calif.) using t-Boc amino acids and peptidylglycine a-aminating monooxygenase resins as described (D'Souza et al., *J. Biol. Chem.*, 263:3943-3951, 1988). Deprotection reactions for releasing the peptides from the solid-phase support were performed by treating the peptide on the matrix with anhydrous hydrogen fluoride containing 10% thioanisole for 1 hr at 0° C. Cleaved peptides were purified by high performance liquid chromatography on a C18-ODS2 column. Elution was performed with a 0-80% linear gradient of acetonitrile containing 0.1% trifluoroacetic acid. The final amino acid composition of the peptides was confirmed by amino acid analysis. The peptides used in this study are shown in Table 1.

TABLE 1

| | | GPIIIa Peptides | |
|---|---|---|---|
| Designation | GPIIIA Location* | SEQ ID NO | Amino Acid Sequence[1] |
| P1 | (93-103) | 10 | RPDDSKNFSIQ |
| P2 | (118-128) | 11 | MDLSYSMKDDL |
| P3 | (154-165) | 12 | GAFVDKPVSPYM |
| P4 | (400-417) | 13 | EAKVRGCPQEKEKSFTIK |
| P5 | (561-573) | 14 | TTRTDTCMSSNGL |
| P6 | (636-654) | 15 | RDEIESVKELKDTGKDAVN |
| P7 | (669-680) | 16 | YYEDSSGKSILY |
| P8 | (721-744) | 1 | YHDRKEFAKFEEERARAKWDTANN |
| P9 | (742-762) | 2 | ANNPLYKEATSTFTNITYRGT |
| P10+ | (control) | 17 | ARAKWDTVRDGA |

*The number of the amino and carboxy terminal amino acids are indicated (e.g., P1 begins with GPIIIa amino acid 93 and ends with amino acid 103).
+Amino acid sequence of an unrelated peptide used as a control.
[1]The amino acid residue sequences are shown in single letter code.

Synthesized peptides were solubilized in either phosphate-buffered saline (PBS) or in PBS containing 8 M urea (P8, P9, P10). Preliminary studies showed that each of the peptides bound to plastic and that the urea concentration in the diluted peptide solution used for assay had no affect on the results.

3. Monoclonal Antibodies

Murine monoclonal antibodies against platelet GPIIb (2A9, provided by Dr. V. L. Woods, UCSD) and the gamma heavy chain of human IgG (HB43, American Type Culture Collection, Rockville, Md.) were purified from ascites using the MAPS technique (Biorad, Richmond, Calif.). Radiolabeling of HB-43 was accomplished using the iodogen method.

4. Preparation of Platelet Extract

Type 0 platelets were washed 6 times in 0.05M isotonic citrate buffer, pH 6.2, and then solubilized by incubation for 30 min at 4° C. in 1% Triton-X100 (Sigma Chemical Co., St. Louis, Mo.) in PBS ($10^9$ platelets/ml). Insoluble material was removed by ultracentrifugation.

5. Preparation of Affinity-Purified GPIIb/IIIa

Platelet extract was passed through a column of anti-GPIIb monoclonal antibody (2A9) coupled to Sepharose CL. After extensive washing with PBS, the GPIIb/IIIa complex was eluted with 00.1M diethylamine in 1% octaglucopyranoside (OGP) in PBS, pH 10.0, and immediately dialyzed against o.1M NAP04 containing 1% OGP. Purity was confirmed by SDS-PAGE and the protein concentration was determined.

6. Solid-Phase Radioimmunoassay (RIA)

A. Binding to GPIIIa Peptide

Microtiter wells were activated with 100 μl of 0.1% glutaraldehyde in coating buffer (0.1M NaHCO3, pH 8.3) for 1 hr at room temperature (RT). Wells were washed twice with PBS and then incubated for 2 hr at RT with 1 μg of each synthetic peptide in 100 μl of coating buffer. After 6 washes with 0.05% Tween-20 (Sigma Chemical Co., St. Louis, Mo.) in PBS (wash buffer), each well was incubated with 200 μl of 2% BSA in wash buffer for 1 hr at RT. The wells were washed 6 times, followed by the addition to triplicate wells of 100 μl of plasma diluted 1/10 in wash buffer. After incubation for 1 hr and 6 washes, 100 μl of radiolabeled anti-human IgG in wash buffer (100,000 cpm) was added to each well. After a final 1 hr incubation and 6 washes, well-bound radioactivity was determined. Data were expressed as a ratio: Mean cpm bound to GPIIIa peptide divided by mean cpm bound to control peptide (P10).

Nine synthetic peptides corresponding to different sequences within platelet GPIIIa (P1–P9, Table 1) were used as antigenic targets. A synthetic peptide of human HLA Class I heavy chain was used as a control (P10). Plasma from 13 patients with chronic ITP was studied. When compared to plasma from 19 normal subjects, plasma autoantibodies from 5 of these patients (ITP-1 to -5) bound significantly ($p<0.001$) to epitopes on either peptide 8 or 9 (FIG. 1). These 2 hydrophilic overlapping peptides are located at the carboxyterminal region of GPIIIa and together comprise the portion of the molecule considered to be the cytoplasmic domain. Plasma for patients ITP-1 and ITP-2 bound to peptide 9 with mean ratios of 32.4 (3 studies) and 5.8 (2 studies), respectively, while patient ITP-3 plasma bound to both peptides 8 and 9 (mean ratios of 13.3 and 3.3, respectively; 3 studies) and patients ITP-4 and ITP-5 bound to peptide 8 (mean ratios of 3.6, 2 studies and 9.4, 2 studies). Samples from the other 8 chronic ITP patients (ITP-6 through ITP-13), 5 patients with alloantibodies (three with anti-P1A1, 1 with thrombasthenia and anti-GPIIb/IIIa antibody, 1 with anti-HLA), and 4 patients with nonimmune thrombocytopenia showed no significant binding to the GPIIIa peptides employed.

B. Binding to GPIIb/IIIa

Autoantibody binding to both affinity-purified GPIIb/IIIa and to GPIIb/IIIa from platelet lysate immobilized by monoclonal antibody (2A9) were studied. In the former case, triplicate wells were coated for 1 hr with 100 μl of affinity-purified GPIIb/IIIa (10 μg/ml) followed by 6 washes and blocking with BSA as described above. For the latter assay, 100 μl of murine anti-GPIIb (2A9) at 10 μg/ml was added to each well. After incubation for 2 hr at RT and washing 6 times, wells were blocked with 2% BSA in wash buffer. Then 100 μl of platelet lysate diluted 1/10 with wash buffer was added to each well and incubated for 1 hr. After washing 6 times, each of these modified assays were completed as described above.

7. Binding to Platelets

Washed platelets ($3\times10^7$) were incubated with patient plasma (ITP-1–15 μl, ITP-2–60 μl, ITP-3–30 μl) in a total volume of 200 μl citrate buffer for 2 hrs at room temperature, followed by 4 washes. After resuspension in 300 μl of citrate buffer, platelets were lysed with 33 μl of 10% Triton X-100 in citrate buffer. Next, 100 μl of lysate was added to wells coated with murine anti-GPIIb. Bound antibody was detected with labeled anti-human IgG as described.

8. Inhibition Studies

To evaluate the ability of washed platelets, affinity-purified GPIIb/IIIa or synthetic peptides to block autoantibody binding, serial dilutions of platelets, GPIIb/IIIa or synthetic peptides (maximum addition: $10^{10}$ platelets, 200 μg GPIIb/IIIa or 10 μg of peptide per 100 μl plasma, respectively) were incubated overnight at 4° C. with the patient's plasma. The preincubated plasma (100 μl 11/10 dilution) was added to replicate wells containing either GPIIb/IIIa from platelet lysate, affinity-purified GPIIb/IIIa or synthetic peptide, and antibody binding to each well was evaluated as describe above. Data were expressed as a percent of the binding of untreated plasma (% inhibition).

Three of the peptide-positive plasma samples (ITP-1, -2 and -3) were tested further; additional testing of ITP-4 and ITP-5 was not possible due to insufficient plasma. For the inhibition experiments, we used plasma concentrations which did not saturate the antigen-coated wells, which in each case was a 1/10 dilution.

Figure 2B:
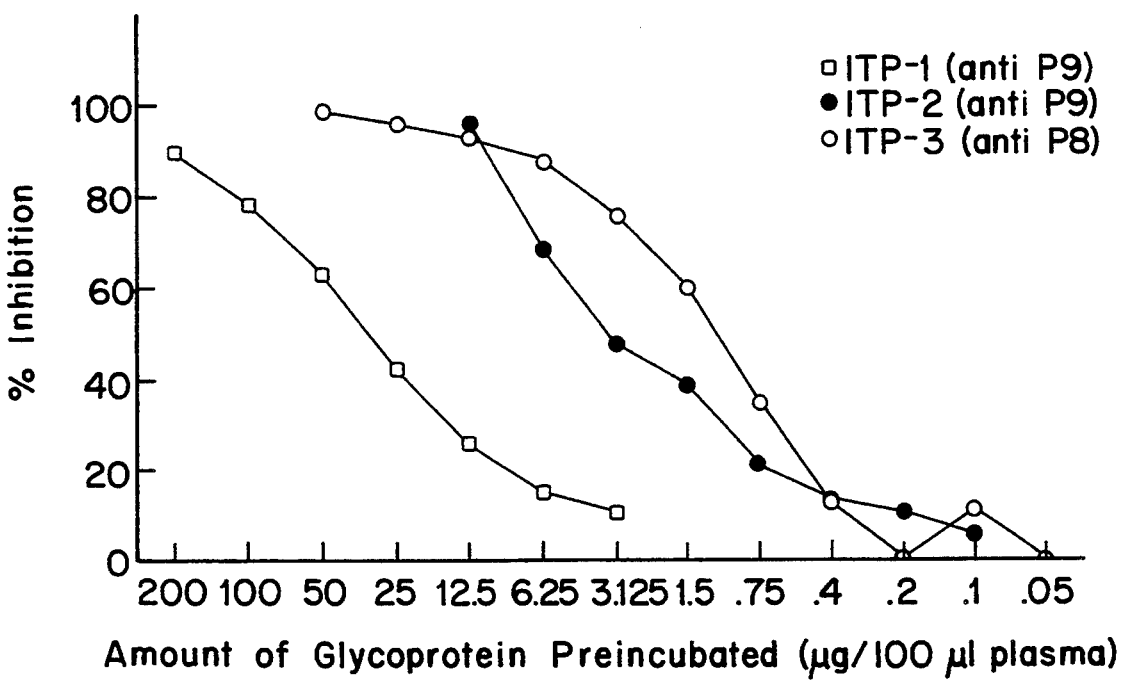

A. Inhibition of Antipeptide Antibody Binding to Peptides by Platelets or Purified GPIIb/IIIa Antibody reactivity of plasma from ITP-1, -2 and -3 with the GPIIIa peptides was completely inhibited by preincubation of plasma with type O washed platelets (FIG. 2A) or affinity-purified GPIIb/IIIa (FIG. 2B) indicating that each of the epitopes was present on both intact washed platelets and purified GPIIb/IIIa.

B. Inhibition of Autoantibody Binding to Peptide, Platelets, and GPIIb/IIIa by Peptides in Solution To evaluate the contribution of these antipeptide antibodies to the patients' total plasma anti-GPIIb/IIIa activity, the ITP plasmas were preincubated with serial dilutions of the appropriate peptide (8 or 9) and then tested in 4 different assays. In the first, the pretreated plasma was incubated with platelets. After washing and lysis, the GPIIb/IIIa complexes were captured on microtiter wells by monoclonal antibody. In the other 3 assays, pretreated plasma was added to microtiter wells coated directly with either peptide or affinity-purified GPIIb/IIIa (affi-GPIIb/IIIa) or to microtiter wells with GPIIb/IIIa from platelet lysate immobilized by monoclonal antibody (moAb-GPIIb/IIIa). Antibody binding was detected in all assays with labeled antihuman IgG.

(i) Inhibition of Binding to Peptide

In all 3 cases, preincubation of plasma with the appropriate peptide resulted in >95% inhibition of antibody binding to immobilized peptide (data not shown).

(ii) Inhibition of Binding to Platelets

Figure 3:
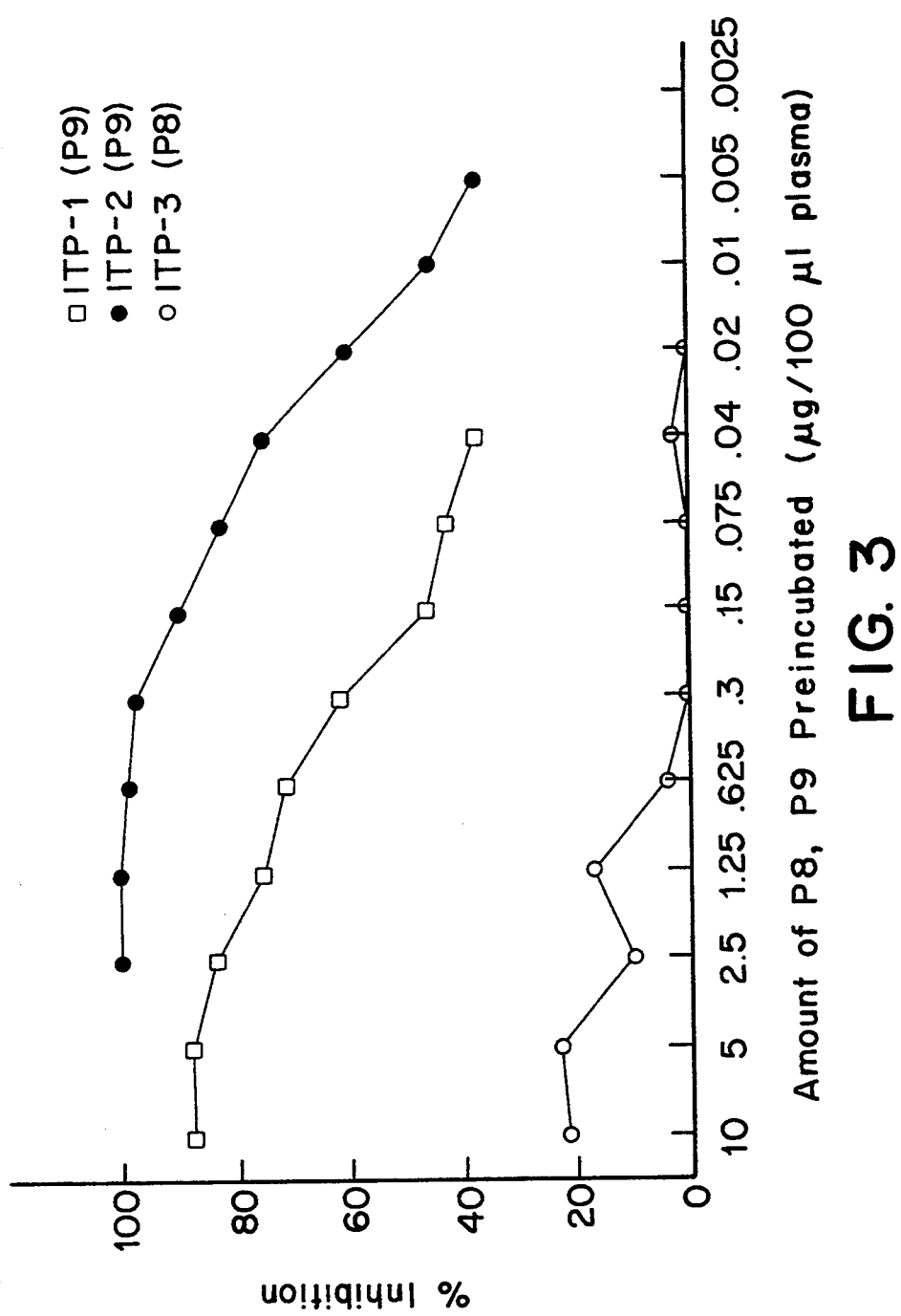
FIG. 3 illustrates inhibition of autoantibody binding to platelets by peptide. Plasma from patients ITP 1-3 was preincubated with the appropriate peptide (P8 or P9) and then with washed intact platelets. After washing, the immune complexes were captured or microtiter wells coated with monoclonal anti-GPIIb/IIIa and autoantibody detected with labeled antihuman IgG. Results are expressed as the % inhibition.

Preincubation with peptide 9 resulted in almost complete inhibition of the binding of ITP-1 [87.8–98.0), 3 studies] and ITP-2[94.0% (87.9–100), 2 studies] autoantibodies to washed platelets while peptide 8 only partially blocked [19.7% (17.7–21.6), 2 studies] the binding of ITP-3 autoantibodies (FIG. 3).

(iii) Inhibition of Binding to GPIIb/IIIa

Figure 4A:
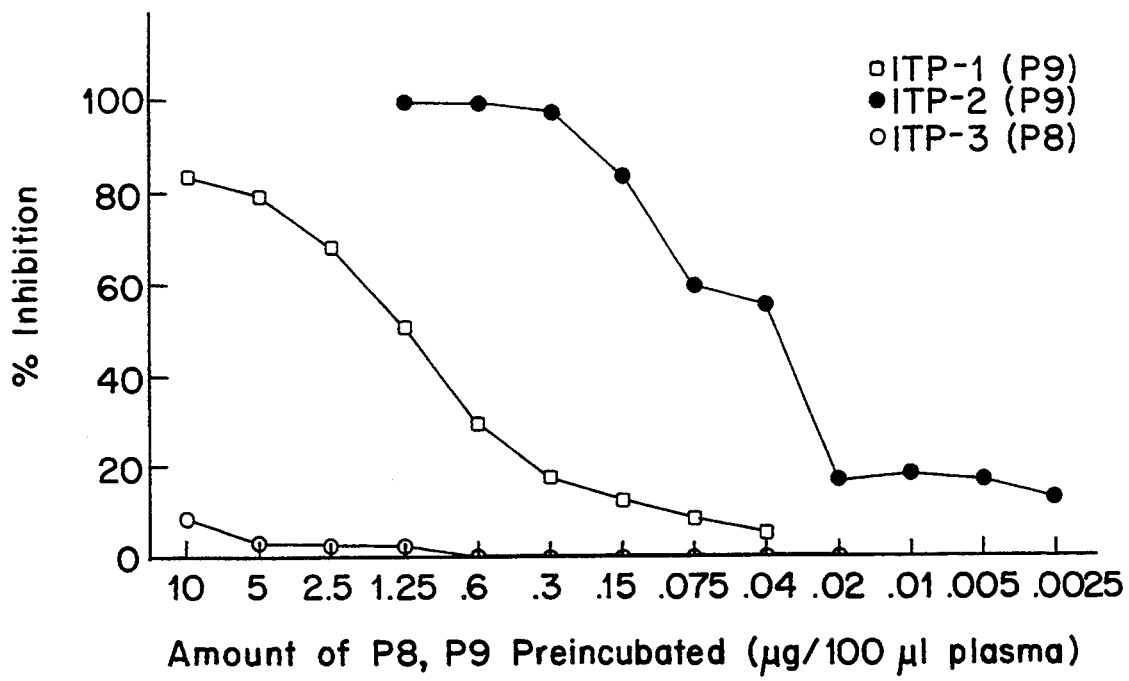
FIGS. 4A and 4B illustrate inhibition of autoantibody binding to GPIIb/IIIa by peptide (P8 or P9) and then added to wells containing GPIIb/IIIa from platelet lysate immobilized with monoclonal antibody (FIG.) or to wells coated with affinity-purified GPIIb/IIIa (FIG.). Autoantibody was detected using antihuman IgG. Results are expressed as the % inhibition.
Figure 4B:
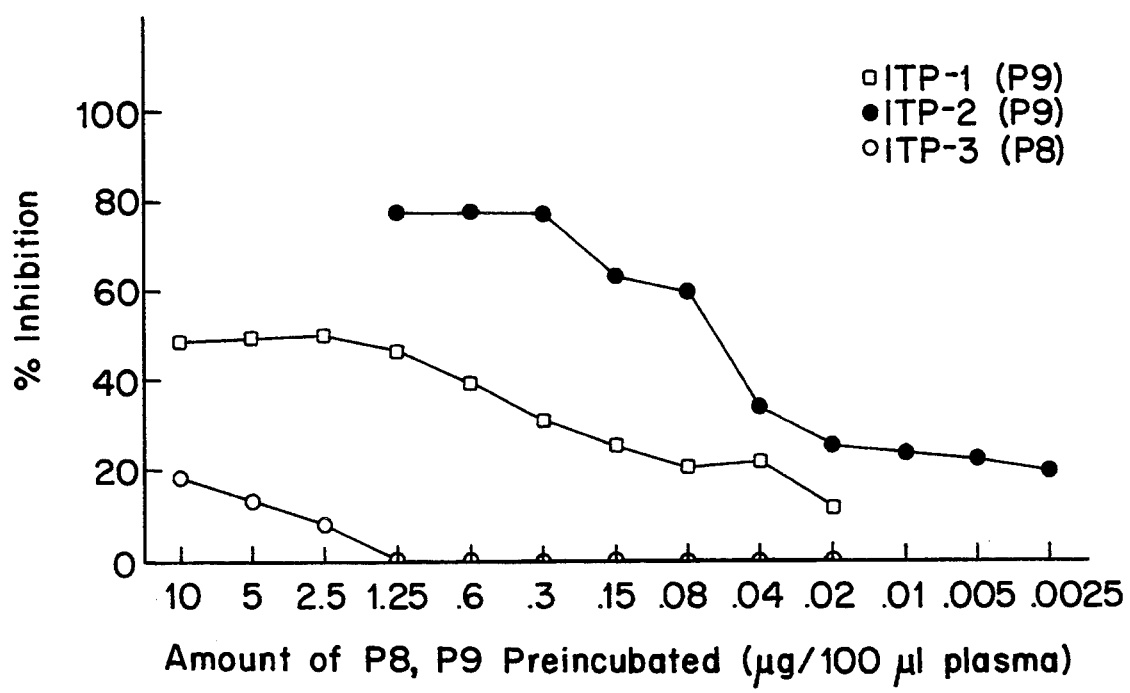

Preincubation of plasma from ITP-1, -2 and -3 with peptide resulted in maximum mean inhibition of binding to Moab-GPIIb/IIIa of 86.8% (83.7–89.8, 2 studies), 100% (2 studies) and 12.5% (8.6–16.3, 2 studies), respectively. On the other hand, studies using affi-GPIIb/IIIa as the target antigen gave somewhat different results. Peptide pretreatment resulted in the following % maximal inhibition: ITP-1—54.9% (48.7–62.7, 3 studies), ITP-2—87.5% (1 study) and IT-3—35.4% (19.4–49.3, 3 studies). Examples are shown in FIGS. 4A and 4B.

9. Preparation of Chinese Hamster Cell Recombinants

Full-length cDNAs for GPIIb, GPIIIa (O'Toole et al., Blood, 74:14–18, 1989), and a cDNA for GPIIIa lacking nucleotides which encode for the carboxyterminal region amino acids 728 to 762 was subcloned into the eukaryotic expression vector CDM8 (Aruffo et al., Proc. Natl. Acad. Sci. USA, 84:8573–8577, 1987) and used to transfect Chinese hamster ovary (CHO) cells as described (Loftus et al., Science, 249:915–918, 1990). The stable clonal line expressing intact GPIIb/IIIa was designated A5 and was characterized as described (Loftus, et al., Science, 249:915–918, 1990). Those transfected with complete GPIIb and the truncated GPIIIa lacking the 35 carboxy-terminal amino acids were designated IIb$\beta_3\Delta$728. In FACS assays, these cells reacted with a previously described panel of murine monoclonal anti-GPIIb-IIIa antibodies, including one which was complex specific (O'Toole et al., Blood, 74:14–18, 1989). Untransfected CHO cells were used as controls. Cells were washed 3 times in 3.5 mm EDTA in PBS and once in PBS. After resuspension in PBS ($2 \times 10^7$/ml), the cells were lysed by 1% Triton X-100 and ultracentrifuge at 100,000×G for 30 minutes. The supernatant was removed and used for solid-phase RIA as GPIIb/IIIa antigen immobilized on microtiter wells by anti-GPIIb/IIIa monoclonal antibody. The binding of plasma antibody to the recombinant GPIIb/IIIa was detected as described above.

The binding of plasma from 5 chronic ITP patients to either peptide 8 or 9 suggested that this region was an important target for autoantibodies in chronic ITP. To establish that the portion of the GPIIIa molecule containing these sequences was required for autoantibody recognition, autoantibody binding to GPIIb/IIIa obtained from Chinese Hamster cells expressing either intact human recombinant GPIIb/III complex (A5 cells) or the GPIIb/IIIa complex lacking the region containing peptides 8 and 9 (II$_b\beta_3$ 728 cells) was compared. In 10 of the 13 chronic ITP patients tested, greater than 75% of the binding to GPIIb/IIIa was dependent on the presence of the presumptive cytoplasmic domain containing peptides 8 and 9 (Table 2). Binding of anti-PLA1 alloantibodies [known to be due to a polymorphism in the extracellular domain of the GPIIIa molecule (Newman, et al., J. Clin. Invest, 83:1778–1781, 1989)] to A5 and II$_b\beta_3$ 728 cells was identical. Similarly, plasma from 3 of 13 chronic ITP patients (ITP-11, -12 and -13) and 1 thrombasthenic patient with anti-GPIIb/IIIa alloantibody gave similar binding to A5 and II$_b\beta_3$ 728 cells was identical. Similarly, plasma from 3 of 13 chronic ITP patients (ITP-11, -12 and -13) and 1 thrombasthenic patient with anti-GPIIb/IIIa alloantibody gave similar binding to A5 and II$_b\beta_3$ 728.

TABLE 2

Antiplatelet Antibody Binding to Recombinant GPIIb/IIIa in Chinese Hamster Cells

| Patient* | Tx-Preg** | Anti-Peptide Antibody[+] Result | Antigen | Binding to Chinese Hamster Cells[#] (Net cpm) A5 | II$_b\beta_3$ 728 | % Binding[++] |
|---|---|---|---|---|---|---|
| ITP-1 | − − | POS | P9 | 37,116 | 0 | 0 |
| ITP-2 | + + | POS | P9 | 8,912 | 0 | 0 |
| ITP-3 | + − | POS | P8, 9 | 28,625 | 5,604 | 19.6 |
| ITP-4 | − + | POS | P8 | 20,637 | 0 | 0 |
| ITP-5 | + + | POS | P8 | 2,308 | 0 | 0 |
| ITP-6 | + + | NEG | — | 14,034 | 0 | 0 |
| ITP-7 | + + | NEG | — | 4,707 | 476 | 10.1 |
| ITP-8 | − − | NEG | — | 5,619 | 0 | 0 |
| ITP-9 | + − | NEG | — | 1,296 | 0 | 0 |
| ITP-10 | − + | NEG | — | 4,854 | 0 | 0 |
| ITP-11 | − + | NEG | — | 10,527 | 9,124 | 86.7 |
| ITP-12 | − − | NEG | — | 3,638 | 3,258 | 89.6 |
| ITP-13 | ? ? | NEG | — | 24,977 | 21,063 | 84.3 |
| GZ | | NEG | — | 4,609 | 3,363 | 73.0 |
| PTP-1 | | NEG | — | 46,426 | 44,033 | 94.8 |
| PTP-2 | | NEG | — | 35,798 | 34,322 | 95.9 |
| PTP-3 | | NEG | — | 12,163 | 11,385 | 93.6 |

*ITP - Chronic immune thrombocytopenic purpura; GZ - Glanzmann's thrombasthenia with anti-GPIIb/IIIa alloantibody; PTP - post-transfusion purpura with anti-PL[A1] alloantibody.
**Tx - transfusion; preg - pregnant; + patient transfused or had been pregnant; − no transfusion or pregnancy; ? date not available.
[+]POS - positive for antipeptide antibody; NEG - negative for antipeptide antibody; P8 - peptide 8; P9 - peptide 9.
[#]A5 - Chinese hamster cells expressing recombinant GPIIb/IIIa; II$_b\beta_3$ 728 - Chinese hamster cells expressing GPIIb/IIIa lacking GPIIIA residues 728-762. Data are expressed as net cpm after subtracting radioactivity bound to control Chinese hamster cells.
[++] % Binding = (cpm II$_b\beta_3$ 728 minus cpm control cells ÷ cpm A5 minus cpm control cells) × 100.

10. Discussion of the Results of Examples 1–9

Most antiplatelet autoantibodies in chronic ITP are directed towards either the platelet GPIIb/IIIa or GPIb/IX complex (McMillan et al., Blood, 70:1040–1045, 1987). In many instances, the antigenic sites on the GPIIb/IIIa complex are localized to GPIIIa (Beardsley et al., J. Clin. Invest., 74:1701–1707, 1984).

In this study, it was shown that plasma from 5 of the 13 selected chronic ITP patients binds to either synthetic GPIIIa peptides 8 (3 patients) or 9 (2 patients). These two peptides together form most of the carboxyterminal region of GPIIIa which is presumed to be the cytoplasmic domain. Of the 3 patients tested further (ITP-1, -2 and -3), binding to the synthetic peptide (P8 or P9) was completely inhibited by preincubating plasma with the appropriate peptide, showing the specificity of the antibody binding and reactivity with the antigen not only on solid support but also in solution. Furthermore, the antibody binding to each peptide was also inhibited completely by preincubation with washed platelets or with purified GPIIb/IIIa indicating that the antipeptide antibodies react with the whole GPIIb/IIIa molecule as well as GPIIIa on the platelet surface.

Preincubation of plasma from 2 patients (ITP-1 and ITP-2) with peptide (P9) resulted in >80% inhibition of antibody binding to both platelets and GPIIb/IIIa from platelet lysates whereas P8-treated plasma from patient ITP-3 produced less than 30% inhibition. Peptide inhibition of binding to affinity-purified GPIIb/IIIa was less complete than that seen using platelet lysate-derived GPIIb-IIIa, suggesting that some alteration of the GPIIb/IIIa molecule occurred during the purification procedure or trace contaminants interfered with the assay. From these results, we conclude that antibodies directed against the carboxyterminal region (P9) in patients ITP-1 and ITP-2 comprise the main component of the plasma anti-GPIIb/IIIa autoantibodies, while antibodies to P8 in patient ITP-3 either represent a minor portion of the circulating autoantibodies or the epitope lies within the overlapping region of P8 and P9 as suggested by the binding by this antibody to both P8 and P9 (P8>P9).

To further explore autoantibody binding to the carboxyterminal region of GPIIIa, CHO cells were transfected with GPIIb and either the sole GPIIIa molecule or the GPIIIa molecule lacking amino acids 728 and 762 (includes peptides 8 and 9). Ten of the 13 chronic ITP plasmas required the presence of the carboxyterminal domain for maximal binding, including all 5 patients with binding to peptides 8 and 9, and 5 additional patients who showed no binding to the peptides. It seems likely that the plasma from these latter 5 patients binds to other epitopes of the presumed cytoplasmic domain although it is possible that the absence of this portion of the molecule may perturb the conformation of the remaining molecule and preclude antibody binding. In addition to confirming the epitope specificity in the patients with positive antipeptide antibody, these results provide strong evidence that the carboxyterminal region is an important area for stimulating antiplatelet autoantibody formation in chronic ITP patients. Obviously, there are other important antigenic regions as demonstrated by the equal binding of the other ITP autoantibodies as well as alloantibodies to GPIIb-IIIa (anti-P1A1, known to bind to the amino terminal region of GPIIIa, and anti-GPIIb/IIIa from a thrombasthenic patient) to both the intact and truncated recombinant GPIIIa molecules.

The pathogenetic role of autoantibodies directed against the carboxyterminal region of GPIIIa is not known. Since this region is preceded by the putative transmembrane domain, it has been considered cytoplasmic and should not be available for antibody binding. However, our studies on patients ITP-1 and -2 demonstrate that autoantibodies directed to the carboxyterminal region are absorbed by washed platelets and autoantibody binding to washed platelets can be inhibited by peptide 9. These results suggest that a least a portion of the putative cytoplasmic domain is expressed upon the surface of washed platelets. Whether this expression is present in vivo or merely reflects perturbations during platelet washing remains to be determined.

There are alternative explanations for the presence of autoantibodies to the "cytoplasmic domain" in chronic ITP patients. Antigens may be expressed during the course of platelet destruction by antibodies against surface determinants which result in autoantibody formation against these cytoplasmic antigens. Alternatively, since the putative cytoplasmic domains of integrins are highly conserved between species (Marcantonio et al., *J. Cell. Biol.*, 106:1765–1772, 1988), it is possible that the immune response to this region of GPIIIa is triggered by exposure to a homologous sequence from a lower organism or from a cell other than the platelet. Finally, the possibility that the antibodies against the cytoplasmic domain in some of these patients could be alloantibodies must be considered although this is not possible in patients ITP-1 and ITP-8 who were neither transfused nor pregnant (Table 2).

In summary, the present studies show that autoantibodies in some patients with chronic ITP bind to the putative cytoplasmic domain of platelet GPIIIa and that, in 2 of the patients, anti-P9 antibody represented the major portion of the detectable circulating anti-GPIIb/IIIa autoantibodies. The role of this type of autoantibody in the pathogenesis of chronic ITP remains to be determined.

11. Preparation of Fusion Proteins Containing GPIIIa Polypeptides

To further characterize the region of GPIIIa important in recognition of autoantibodies in ITP patient antisera, fusion proteins were constructed containing portions of GPIIIa fused to maltose binding protein. Two constructs were prepared as maltose binding fusion proteins: one containing residues 1–200 of GPIIIa and another containing residues 690–762 of GPIIIa.

To that end, oligonucleotide primer pairs containing the recited GPIIIa DNA sequences were synthesized using standard oligonucleotide synthesis, having lengths of about 20–24 nucleotides and including recognition sequences for XbaI on one primer and for HindIII on the other primer of the pair. The primer pair is used in a polymerase chain reaction (PCR) as is well known to produce a target DNA molecule flanked by the indicated restriction endonuclease sites which encodes the indicated GPIIIa nucleotide sequence that is in frame with a preselected maltose binding protein (MBP) when the target DNA molecule is inserted into an expression vector that encodes MBP. The vector, pIH821 (New England Biolabs, Beverly, Mass.), expresses the cloned coding sequences of GPIIIa in the form of a fusion protein with MBP when the assembled vector in *E. coli*. The MBP fusion protein system has been described by Maina et al, *Gene*, 74:365–373 (1988). The pIH821 vector places the MBP protein and the insert-encoded protein in a fusion configuration separated by a Factor Xa cleavage site. The expressed GPIIIA-MBP fusion protein can be affinity purified on an amylose column, and the purified fusion protein can be cleaved using Xa to release the GPIIIa portion from MBP.

A. PCR procedure to clone GPIIIa Fragments

A full length cDNA clone encoding GPIIIa was provided by Dr. O'Toole (The Scripps Research Institute, La Jolla, Calif.), and the clone and the complete nucleotide sequence is described by O'Toole et al., *Blood*, 74:14–18 (1989).

A PCR reaction mixture was prepared in buffer (pH 8.3) containing 50 mM KCl, 10 mM Tris-Cl, 1.5 mM MgCl$_2$, two oligonucleotide primers (1 μM) corresponding to sense and anti-sense strands of Fn at positions corresponding to residues 690-762, a mixture of four dNTPs (200 μM each), template GPIIIa cDNA (10-100 ng in 10 mM Tris-Cl, pH 7.6; 0.1 mM EDTA, pH 8.0), and Taq polymerase (2 units). The mixture was overlaid with mineral oil and amplification was carried out in a DNA Thermal Cycler programmed to permit denaturation at 94° C., annealing at 50° C. and chain extension at 72° C. Times for denaturation, annealing and polymerization for the first cycle, midcycles and last cycles, respectively were as follows: denaturation (5, 1, 1 minute), annealing (2, 2 and 2 minutes) and polymerization (3, 3, and 10 minutes). The reaction was repeated for a total of 30 cycles to produce a PCR product.

The PCR product was analyzed on 1.2% agarose gels, the band containing a fragment corresponding to 690-762 was excised and the DNA recovered by electroelution. The DNA fragment and plasmid vector pIH821 (New England Biolabs, Inc., Beverly, Mass.) were prepared for ligation by restriction enzyme digestion. A different restriction enzyme recognition site was incorporated on each end of the PCR product (DNA fragments) to assure correct orientation in the vector. After DNA purification, ligation was accomplished by incubating 100 ng of DNA fragment with 200 ng vector DNA in 0.1% BSA-0.05M Tris-Cl buffer, pH 7.8 containing 1 mM ATP, 20 mM dithiothreitol, 5 mM $MgCl_2$ followed by the addition of 1 unit of Bacteriophage T4 ligase. To incorporate the DNA-containing plasmids into DH5a $E.$ $coli$, an aliquot of the ligation mixture (25-50 ng DNA in 5 μl) was incubated with $E.$ $coli$, (DH5a have been made competent for DNA uptake) for 30 minutes on ice followed by heating to 42° C. for 90 seconds and then chilling on ice for 2 minutes. To the mixture was added 90 μl of 0.2% glucose in SOB medium followed by incubation for 45 minutes at 37° C. Next, 100-200 μl was spread on NZY top agar with ampicillin. Positive ampicillin-resistant colonies were identified by the annealing of $^{32}P$-labeled PCR fragments to nitrocellulose lifts.

To document the presence of the GPIIIa DNA fragment insert, representative positive colonies were harvested and inoculated separately into 2 ml of NZY media containing ampicillin (100 μg/ml) and incubated O.N. at 37° C. A 1.5 ml aliquot of each was centrifuged and the pellet was lysed in 100 μl of 500 mM glucose, 10 mM EDTA in 0.025 M Tris-Cl, pH 8 by adding sequentially: 200 μl of 0.2N NaOH, 1% SDS-incubate 5 minutes; 150 μl 3M KCl, 5M acetate-incubate 5 minutes. After centrifugation, the supernatant DNA was purified by phenol/chloroform extraction and ethanol precipitation, digested with the appropriate restriction enzyme(s) and run on a 1.2% agarose gel. $E.$ $coli$ containing the DNA fragments exhibited bands of expected size (maltose binding protein and DNA fragment). The $E.$ $coli$ colony containing DNA fragments corresponding to GPIIIa 690-762 in an MBP fusion protein was selected for later use.

B. Purification of GPIIIa-MBP Fusion

Two ml aliquots of overnight cultures of $E.$ $coli$ containing the DNA insertion of GPIIIa 690-792 prepared above were added to one or more 2 liter flasks containing 500 ml of TY media (10 g/l tryptone, 5 g/l yeast extract, 5 g/l NaCl, 0.2% D-glucose, 50 mg/l ampicillin) and culture growth was optimal (abs.600 of 0.4-0.5), 300 μl of 500 mM IPTG inducer [300 μM]$_F$ was added.

After 30-60 minutes incubation, the cells were chilled and centrifuged for 5 minutes at 15,000×g at 4° C. The cell pellets from each culture were pooled and resuspended in 10 ml of lysis buffer per 500 ml culture [lysis buffer—5 mM phosphate buffer, pH 7, containing 0.25% Tween-20, 30 mM NaCl, 10 mM EDTA, 10 mM EGTA and the following protease inhibitors: Pepstatin A (2.5 μg/ml), Chymostatin (2.5 μg/ml), Leupeptin (10 μM), Benzamidine HCl (10 mM), PMSF (2 mM) and Aprotinin (1.5-3 units] and frozen in a dry ice/ethanol bath. Just prior to use, the cells were rapidly thawed and 200 μg/ml of solid lysozyme was added and the mixture incubated on ice for 15 minutes. After centrifugation for 30 minutes at 4° C. at 20,000×g, the supernatant was diluted 1:4 with 0.25% Tween-20 in column buffer (0.005M phosphate, 500 mM NaCl, 2.5 mM EDTA, pH 7) containing all protease inhibitors but Chymostatin and Pepstatin.

C. Affinity Purification

Amylose resin (New England Biolabs) used according to the supplier's instructions was preswollen and washed in 0.25% Tween-20 in column buffer and then mixed in batch form with the cell lysate followed by 45 minutes incubation at 4° C. After 5 washes at 4° C. with 0.25% Tween-Column buffer and 5 washes with column buffer alone, the maltose binding protein fusion product was eluted from the gel by incubation with an equal volume of 10 mM maltose in column buffer for 30 minutes at 4° C. The eluate was harvested after removal of the resin by slow centrifugation to yield GPIIIa-MBP fusion protein.

The protein concentration was determined and the molecular weight of the protein bands and the degree of degradation were evaluated by SDS-PAGE. The presence of the maltose binding protein and GPIIIa fragment was documented with immunoblots using appropriate antibodies.

The produced GPIIIa-MBP fusion proteins containing residues 1-200 or residues 690-762 were analyzed using direct binding in a RIA assay according to the procedure described in Example 6A, except that the fusion protein was coated on the plates in place of synthetic polypeptides. By the RIA assay, 4 ITP patient plasma shown previously to immunoreact with polypeptides P9, identifying a portion of the cytoplasmic domain of GPIIIa, immunoreacted with the GPIIIa-MBP fusion protein that contains residues 690-762 of GPIIIa. In the RIA assay, 2 anti-P1A1 antigen antibodies immunoreacted with the GPIIIa-MBP fusion protein that contains residues 1-200 of GPIIIa, which contains the P1A1 antigen. These data show that the GPIIIa-MBP fusion proteins produced above contain GPIIIa polypeptide-defined determinants that are immunoreactive with antibodies in the form of a fusion protein. Thus the data identifies additional polypeptide-defined regions of GPIIIa, and therefore polypeptides, useful in the present invention as reagents for the detection of anti-GPIIIa antibodies, namely, residues 1-200 and residues 690-762 of GPIIIa.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Tyr His Asp Arg Lys Glu Phe Ala Lys Phe Glu Glu Glu Arg Ala Arg
1               5                   10                  15

Ala Lys Trp Asp Thr Ala Asn Asn
            20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:2:

```
Ala Asn Asn Pro Leu Tyr Lys Glu Ala Thr Ser Thr Phe Thr Asn Ile
1               5                   10                  15

Thr Tyr Arg Gly Thr
            20
```

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:3:

```
Tyr His Asp Arg Lys Glu Phe Ala Lys Phe Glu Glu Glu Arg Ala Arg
1               5                   10                  15

Ala Lys Trp Asp Thr Ala Asn Asn Ala Asn Asn Pro Leu Tyr Lys Glu
            20                  25                  30

Ala Thr Ser Thr Phe Thr Asn Ile Thr Tyr Arg Gly Thr
        35                  40                  45
```

( 2 ) INFORMATION FOR SEQ ID NO:4:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:4:

```
Ile His Asp Arg Lys Glu Phe Ala Lys Phe Glu Glu Glu Arg Ala Arg
1               5                   10                  15

Ala Lys Trp Asp Thr Ala Asn Asn Pro Leu Tyr Lys Glu Ala Thr Ser
            20                  25                  30

Thr Phe Thr Asn Ile Thr Tyr Arg Gly Thr
            35                  40
```

( 2 ) INFORMATION FOR SEQ ID NO:5:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:5:

```
Gly Pro Asp Ile Leu Val Val Leu Leu Ser Val Met Gly Ala Ile Leu
1               5                   10                  15

Leu Thr Gly Leu Ala Ala Leu Leu Ile Trp Lys Leu Leu Ile Thr Ile
            20                  25                  30

His Asp Arg Lys Glu Phe Ala Lys Phe Glu Glu Glu Arg Ala Arg Ala
            35                  40                  45

Lys Trp Asp Thr Ala Asn Asn Pro Leu Tyr Lys Glu Ala Thr Ser Thr
    50                  55                  60

Phe Thr Asn Ile Thr Tyr Arg Gly Thr
65                  70
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Region
        ( B ) LOCATION: 1
        ( D ) OTHER INFORMATION: /note="Xaa represents a spacing
           segment which may/may not be present and whose
           sequence may differ each time it is used."

(i x) FEATURE:
    (A) NAME/KEY: Region
    (B) LOCATION: 26
    (D) OTHER INFORMATION: /note="Xaa represents a spacing
        segment which may/may not be present and whose
        sequence may differ each time it is used."

(x i) SEQUENCE DESCRIPTION: SEQ ID NO:6:

Xaa  Tyr  His  Asp  Arg  Lys  Glu  Phe  Ala  Lys  Phe  Glu  Glu  Arg  Ala
1                   5                        10                       15

Arg  Ala  Lys  Trp  Asp  Thr  Ala  Asn  Asn  Xaa
               20                       25

(2) INFORMATION FOR SEQ ID NO:7:

(i) SEQUENCE CHARACTERISTICS:
        (A) LENGTH: 23 amino acids
        (B) TYPE: amino acid
        (D) TOPOLOGY: linear (i i) MOLECULE TYPE: peptide (i i i) HYPOTHETICAL: NO (i v) ANTI-SENSE: NO (v) FRAGMENT TYPE: C-terminal (i x) FEATURE:
        (A) NAME/KEY: Region
        (B) LOCATION: 1
        (D) OTHER INFORMATION: /note="Xaa represents a spacing
            segment which may/may not be present and whose
            sequence may differ each time it is used."

(i x) FEATURE:
        (A) NAME/KEY: Region
        (B) LOCATION: 23
        (D) OTHER INFORMATION: /note="Xaa represents a spacing
            segment which may/may not be present and whose
            sequence may differ each time it is used."

(x i) SEQUENCE DESCRIPTION: SEQ ID NO:7:

Xaa  Ala  Asn  Asn  Pro  Leu  Tyr  Lys  Glu  Ala  Thr  Ser  Thr  Phe  Thr  Asn
1                   5                        10                       15

Ile  Thr  Tyr  Arg  Gly  Thr  Xaa
               20

(2) INFORMATION FOR SEQ ID NO:8:

(i) SEQUENCE CHARACTERISTICS:
        (A) LENGTH: 44 amino acids
        (B) TYPE: amino acid
        (D) TOPOLOGY: linear (i i) MOLECULE TYPE: peptide (i i i) HYPOTHETICAL: NO (i v) ANTI-SENSE: NO (v) FRAGMENT TYPE: C-terminal (i x) FEATURE:
        (A) NAME/KEY: Region
        (B) LOCATION: 1
        (D) OTHER INFORMATION: /note="Xaa represents a spacing
            segment which may/may not be present and whose
            sequence may differ each time it is used."

(i x) FEATURE:
        (A) NAME/KEY: Region
        (B) LOCATION: 44
        (D) OTHER INFORMATION: /note="Xaa represents a spacing
            segment which may/may not be present and whose sequence may differ each time it is used."

( x i ) SEQUENCE DESCRIPTION: SEQ ID NO:8:

| Xaa | Tyr | His | Asp | Arg | Lys | Glu | Phe | Ala | Lys | Phe | Glu | Glu | Glu | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Ala | Lys | Trp | Asp | Thr | Ala | Asn | Asn | Pro | Leu | Tyr | Lys | Glu | Ala | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Thr | Phe | Thr | Asn | Ile | Thr | Tyr | Arg | Gly | Thr | Xaa |
|-----|-----|-----|-----|-----|-----|-----|-----|-----|-----|-----|-----|
|     |     | 35  |     |     |     |     | 40  |     |     |     |     |

( 2 ) INFORMATION FOR SEQ ID NO:9:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( i x ) FEATURE:
        ( A ) NAME/KEY: Region
        ( B ) LOCATION: 1
        ( D ) OTHER INFORMATION: /note="Xaa represents a spacing
        segment which may/may not be present and whose
        sequence may differ each time it is used."

( i x ) FEATURE:
        ( A ) NAME/KEY: Region
        ( B ) LOCATION: 75
        ( D ) OTHER INFORMATION: /note="Xaa represents a spacing
        segment which may/may not be present and whose
        sequence may differ each time it is used."

( x i ) SEQUENCE DESCRIPTION: SEQ ID NO:9:

| Xaa | Gly | Pro | Asp | Ile | Leu | Val | Val | Leu | Leu | Ser | Val | Met | Gly | Ala | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Leu | Thr | Gly | Leu | Ala | Ala | Leu | Leu | Ile | Trp | Lys | Leu | Leu | Ile | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | His | Asp | Arg | Lys | Glu | Phe | Ala | Lys | Phe | Glu | Glu | Glu | Arg | Ala | Arg |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Lys | Trp | Asp | Thr | Ala | Asn | Asn | Pro | Leu | Tyr | Lys | Glu | Ala | Thr | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Phe | Thr | Asn | Ile | Thr | Tyr | Arg | Gly | Thr | Xaa |
|-----|-----|-----|-----|-----|-----|-----|-----|-----|-----|-----|
| 65  |     |     |     |     | 70  |     |     |     |     | 75  |

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

| Arg | Pro | Asp | Asp | Ser | Lys | Asn | Phe | Ser | Ile | Gln |
|-----|-----|-----|-----|-----|-----|-----|-----|-----|-----|-----|
| 1   |     |     |     | 5   |     |     |     |     | 10  |     |

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:11:

```
Met  Asp  Leu  Ser  Tyr  Ser  Met  Lys  Asp  Asp  Leu
1                   5                        10
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:12:

```
Gly  Ala  Phe  Val  Asp  Lys  Pro  Val  Ser  Pro  Tyr  Met
1                   5                        10
```

( 2 ) INFORMATION FOR SEQ ID NO:13:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:13:

```
Glu  Ala  Lys  Val  Arg  Gly  Cys  Pro  Gln  Glu  Lys  Glu  Lys  Ser  Phe  Thr
1                   5                        10                           15
Ile  Lys
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:14:

-continued

```
Thr  Thr  Arg  Thr  Asp  Thr  Cys  Met  Ser  Ser  Asn  Gly  Leu
1              5                        10
```

( 2 ) INFORMATION FOR SEQ ID NO:15:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

```
Arg  Asp  Glu  Ile  Glu  Ser  Val  Lys  Glu  Leu  Lys  Asp  Thr  Gly  Lys  Asp
1              5                        10                       15
Ala  Val  Asn
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

```
Tyr  Tyr  Glu  Asp  Ser  Ser  Gly  Lys  Ser  Ile  Leu  Tyr
1              5                        10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

```
Ala  Arg  Ala  Lys  Trp  Asp  Thr  Val  Arg  Asp  Gly  Ala
1              5                        10
```

What is claimed is:

1. A method for determining the presence of anti-GPIIIa autoantibodies in a vascular fluid sample, said autoantibodies being indicative of chronic immune thrombocytopenic purpura in a patient, which method comprises:

(a) admixing a vascular fluid sample from a patient with a polypeptide consisting essentially of an amino acid residue sequence corresponding to a formula selected from the group consisting of:

Tyr—His—Asp—Arg—Lys—Glu—Phe—Ala—Lys—Phe—Glu—Glu—Glu—Arg—Ala—Arg—Ala—Lys—Trp—Asp—Thr—Ala—Asn—Asn (SEQ ID NO 1);

Ala—Asn—Asn—Pro—Leu—Tyr—Lys—Glu—Ala—Thr—Ser—Thr—Phe—Thr—Asn—Ile—Thr—Tyr—Arg—Gly—Thr (SEQ ID NO 2);

Ile—His—Asp—Arg—Lys—Glu—Phe—Ala—Lys—Phe—Glu—Glu—Glu—Arg—Ala—Arg—Ala—Lys—Trp—Asp—Thr—Ala—Asn—Asn—Pro—Leu—Tyr—Lys—Glu—Ala—Thr—Ser—Thr—

-continued
Phe—Thr—Asn—Ile—Thr—Tyr—Arg—Gly—Thr
(SEQ ID NO 4); and

Gly—Pro—Asp—Ile—Leu—Val—Val—Leu—Leu—Ser—Val—
Met—Gly—Ala—Ile—Leu—Leu—Thr—Gly—Leu—Ala—Ala—
Leu—Leu—Ile—Trp—Lys—Leu—Leu—Ile—Thr—Ile—His—
Asp—Arg—Lys—Glu—Phe—Ala—Lys—Phe—Glu—Glu—
Arg—Ala—Arg—Ala—Lys—Trp—Asp—Thr—Ala—Asn—Asn—
Pro—Leu—Tyr—Lys—Glu—Ala—Thr—Ser—Thr—Phe—Thr—
Asn—Ile—Thr—Tyr—Arg—Gly—Thr (SEQ ID NO 5), to form an immunoreaction admixture;

(b) maintaining said admixture under biological assay conditions for a period of time sufficient to form an immunoreaction product containing said polypeptide; and
(c) determining the presence of said immunoreaction product, and thereby the presence of said anti-GPIIIa autoantibodies.

2. The method of claim 1, wherein said polypeptide is labeled.
3. The method of claim 1, wherein said polypeptide is affixed to a solid matrix.
4. A diagnostic system in kit form for determining the presence of anti-GPIIIa autoantibodies in a vascular fluid sample comprising, in an amount sufficient for at least one assay, a polypeptide consisting essentially of an amino acid residue sequence corresponding to a formula selected from the group consisting of:

Tyr—His—Asp—Arg—Lys—Glu—Phe—Ala—Lys—Phe—Glu—
Glu—Glu—Arg—Ala—Arg—Ala—Lys—Trp—Asp—Thr—Ala—
Asn—Asn (SEQ ID NO 1);

Ala—Asn—Asn—Pro—Leu—Tyr—Lys—Glu—Ala—Thr—Ser—
Thr—Phe—Thr—Asn—Ile—Thr—Tyr—Arg—Gly—Thr
(SEQ ID NO 2);

Ile—His—Asp—Arg—Lys—Glu—Phe—Ala—Lys—Phe—Glu—
Glu—Glu—Arg—Ala—Arg—Ala—Lys—Trp—Asp—Thr—Ala—
Asn—Asn—Pro—Leu—Tyr—Lys—Glu—Ala—Thr—Ser—Thr—
Phe—Thr—Asn—Ile—Thr—Tyr—Arg—Gly—Thr
(SEQ ID NO 4); and Gly—Pro—Asp—Ile—Leu—Val—Val—Leu—Leu—Ser—Val—
Met—Gly—Ala—Ile—Leu—Leu—Thr—Gly—Leu—Ala—Ala—
Leu—Leu—Ile—Trp—Lys—Leu—Leu—Ile—Thr—Ile—His—
Asp—Arg—Lys—Glu—Phe—Ala—Lys—Phe—Glu Glu—
Arg—Ala—Arg—Ala—Lys—Trp—Asp—Thr—Ala—Asn—Asn—
Pro—Leu—Tyr—Lys—Glu—Ala—Thr—Ser—Thr—Phe—Thr—
Asn—Ile—Thr—Tyr—Arg—Gly—Thr (SEQ ID NO 5).

as a separately packaged reagent.
5. The diagnostic system of claim 4, wherein said polypeptide is labeled.
6. The diagnostic system of claim 4, wherein said polypeptide is affixed to a solid matrix.

* * * * *